(12) United States Patent
Haeusler et al.

(10) Patent No.: US 9,267,872 B2
(45) Date of Patent: Feb. 23, 2016

(54) FLUID PROPERTIES MEASUREMENT DEVICE HAVING A SYMMETRIC RESONATOR

(75) Inventors: Klaus Haeusler, Zurich (CH); Joseph H. Goodbread, Portland, OR (US)

(73) Assignee: RHEONICS GMBH, Winterthur (CH)

( * ) Notice: Subject to any disclaimer, the term of this patent is extended or adjusted under 35 U.S.C. 154(b) by 354 days.

(21) Appl. No.: 13/820,882

(22) PCT Filed: Sep. 6, 2011

(86) PCT No.: PCT/US2011/050571
§ 371 (c)(1),
(2), (4) Date: Mar. 5, 2013

(87) PCT Pub. No.: WO2012/033772
PCT Pub. Date: Mar. 15, 2012

(65) Prior Publication Data
US 2013/0167620 A1      Jul. 4, 2013

Related U.S. Application Data

(60) Provisional application No. 61/380,706, filed on Sep. 7, 2010.

(51) Int. Cl.
*G01N 11/16* (2006.01)
*G01N 11/00* (2006.01)

(52) U.S. Cl.
CPC .............. *G01N 11/162* (2013.01); *G01N 11/16* (2013.01); *G01N 2011/0006* (2013.01)

(58) Field of Classification Search
CPC ..................................................... G01N 11/162
See application file for complete search history.

(56) References Cited

U.S. PATENT DOCUMENTS 3,935,726 A    2/1976  Heinz
5,596,139 A    1/1997  Miura et al.

FOREIGN PATENT DOCUMENTS

JP        03146847 A     6/1991
JP        07072063 A     3/1995

*Primary Examiner* — Paul West
(74) *Attorney, Agent, or Firm* — Timothy E. Siegel Patent Law, PLLC; Timothy E. Siegel

(57) ABSTRACT

A fluid properties measurement device includes a symmetric resonant element having a first mass and a second mass, balanced to the first mass and coupled to the first mass by a torsional spring, having a nodal support between the first mass and the second mass. Also, a chamber having at least one opening accommodates the first mass, free of mechanical constraint and a driving and sensing assembly, is adapted to drive the first mass in torsion and sense resulting torsional movement of the first mass. The torsional spring passes through the opening which is sealed about the torsional spring at the nodal support and the second mass is free to be placed into a fluid, for fluid property measurements.

14 Claims, 4 Drawing Sheets

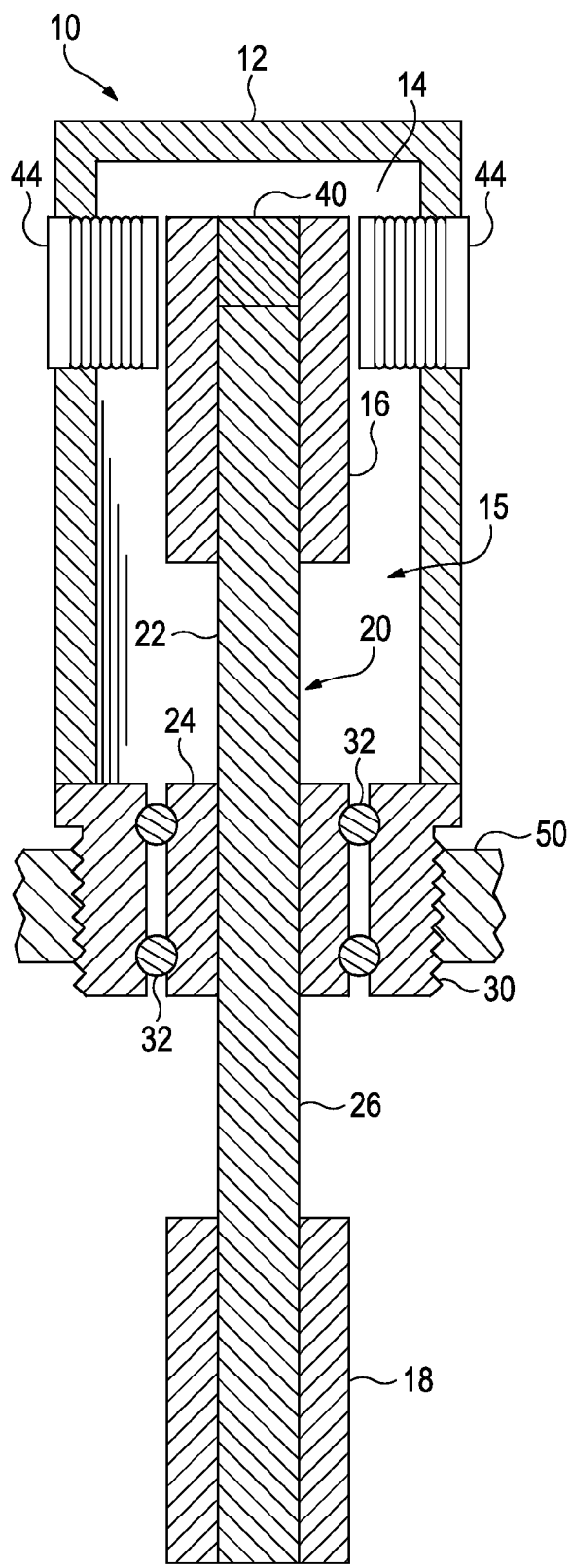
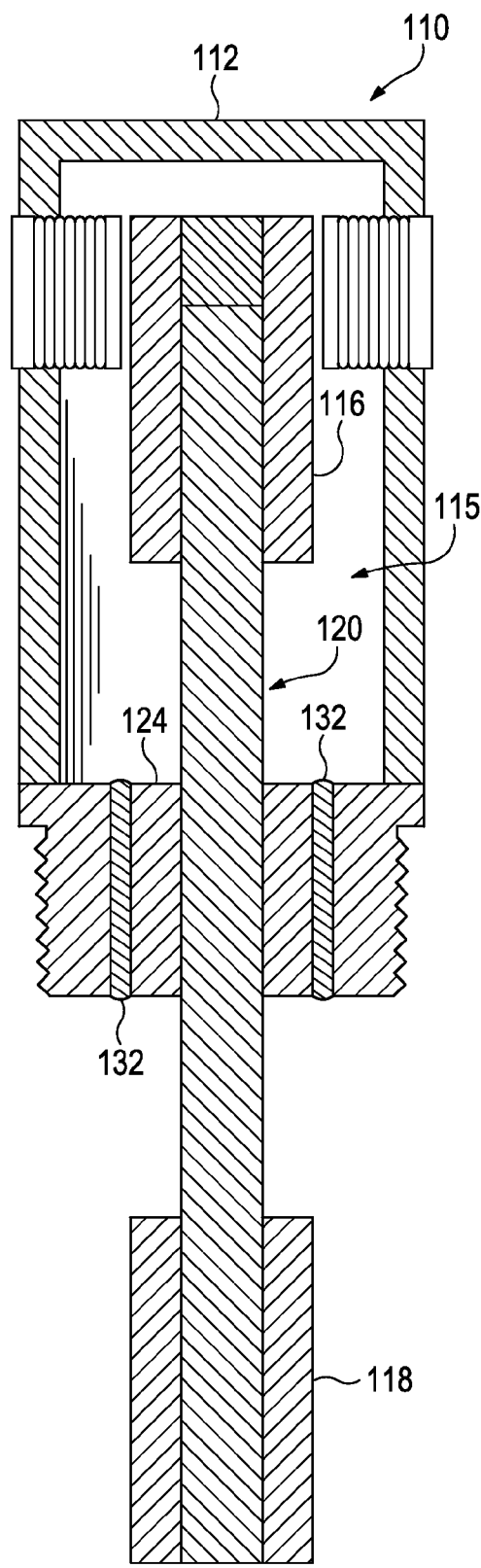
Figure 2
Figure 3

FLUID PROPERTIES MEASUREMENT DEVICE HAVING A SYMMETRIC RESONATOR

BACKGROUND

A viscometer based on the damping of a mechanical resonator can be very accurate in theory, but if installation into a fixed location introduces an unknown and immeasurable amount of intrinsic damping (that is, the amount of damping that the viscometer would experience in a vacuum) then that unknowable quantum of intrinsic damping limits accuracy. The essential problem is that of preventing the vibrations of the viscometer's resonator from leaking into the structure holding the viscometer, for example a pipe or the wall of a tank, thereby affecting the level of intrinsic damping.

Some prior art systems have relied on compliant elements such as elastomeric O-rings to isolate the vibrations to the viscometer structure. Unfortunately, the use of such O-rings limits the pressure and temperature range of viscometer usage, thereby limiting the environments in which such a viscometer can be used. Finally, even if everything about the environment (tank walls, pipe or other holding structure) were known, and O-rings that could accommodate a broad range of temperature and pressure were available, it is very difficult to make the installation process perfectly repeatable. Any time screw threads must be tightened, there is the possibility of variation that can introduce an immeasurable quantum of difference.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a fluid properties measurement device that includes a symmetric resonant element having a first mass and a second mass, balanced to the first mass and coupled to the first mass by a torsional spring, having a nodal support between the first mass and the second mass. Also, a chamber having at least one opening accommodates the first mass, free of mechanical constraint and a driving and sensing assembly, is adapted to drive the first mass in torsion and sense resulting torsional movement of the first mass. The torsional spring passes through the opening which is sealed about the torsional spring at the nodal support and the second mass is free to be placed into a fluid, for fluid property measurements.

In a second separate aspect, the present invention may take the form of a fluid properties measurement device that includes a symmetric resonant element having a first mass and a second mass, balanced to the first mass and coupled to the first mass by a torsional spring, and having a nodal support between the first mass and the second mass. A driving and sensing assembly, adapted to drive the first mass in torsion and sense resulting torsional movement of the first mass. The symmetric resonant element defines a longitudinal passageway from near to the longitudinal end of the second mass to exit point from the first mass and electrical conductors pass through the passageway and out of the exit point. Finally, an electrical temperature measurement device is placed in the second mass and is connected to the electrical conductors, thereby providing an electrical signal reflective of a temperature through the exit point.

In a third separate aspect, the present invention may take the form of a fluid properties measurement device that has a resonator capable of resonating in a preferred anti-symmetric mode, having a first resonant frequency. The device drives the resonator to resonate in a first frequency band about the first resonant frequency. But the resonator may be caused to resonate in a symmetric mode, under some loading scenarios, the symmetric mode having a second resonant frequency that is significantly different from the first resonant frequency. The device detects frequencies within a second frequency band about the second resonant frequency, and stops and restarts the driving of the resonator when a frequency in the second frequency band is detected.

In addition to the exemplary aspects and embodiments described above, further aspects and embodiments will become apparent by reference to the drawings and by study of the following detailed descriptions.

BRIEF DESCRIPTION OF THE DRAWINGS

FIG. 2 is a vertical sectional view of the resonant assembly of FIG. 1.

FIG. 3 is a vertical sectional view of an alternative embodiment of a resonant assembly.

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENT(S)

Figure 1:
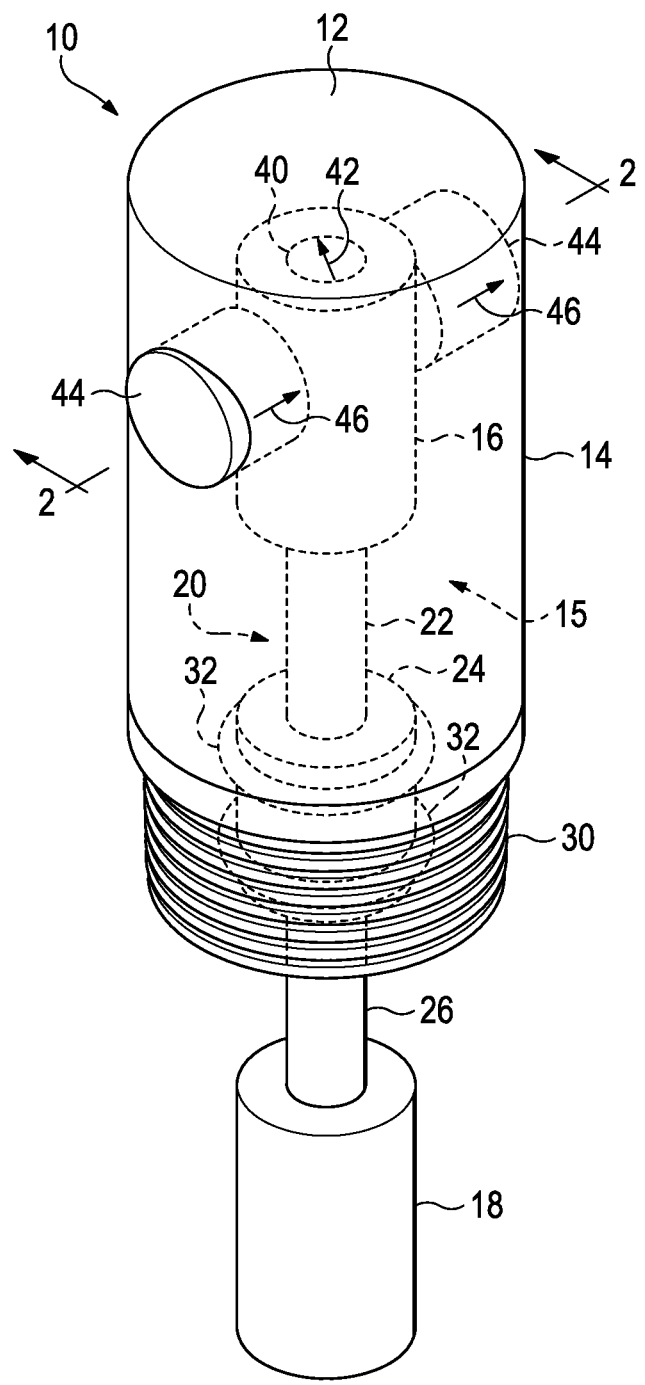
FIG. 1 is a perspective view of a preferred embodiment of a resonant assembly, according to the present invention.

Referring to FIGS. 1 and 2, in a preferred embodiment a resonator assembly 10, which forms the physical portion of a fluid properties measurement device, such as a viscometer, comprises a housing 12 defining a chamber 14. A resonant element 15 is formed from an upper, enclosed mass 16 and a lower, exposed mass 18, which are joined by a torsional spring 20. Torsional spring 20 is made up of an upper torsional spring 22, a nodal support 24 and a lower torsional spring 26. Housing 12 terminates in a threaded element 30 and nodal support 24 is held in place on the interior surface of threaded element 30 by a pair of O-rings 32. The upper mass 16 includes a magnet 40, defining a polarization vector 42 (FIG. 1), which is driven torsionally by a pair of electromagnetic coils 44 defining polarization vector 46 (FIG. 1). The entire resonator assembly may be fitted into a threaded hole in a wall 50 (FIG. 2).

Assembly 10 has the advantage that the resonant element 15 may be removed by sliding it out, and another, similar member may then be installed. Some applications such as use in a corrosive or abrasive particle rich environment, wear down the exposed mass 18, making replacement necessary.

For FIGS. 3-6, all reference numbers for like elements are given the same reference number as in FIG. 2, but with 100, 200, 300 or 400 added, per the formula (FIG. #−2)×100. In a general discussion of the effects of design variations, the reference numbers of FIG. 1 will be taken to apply to reference numbers for all like elements in related embodiments. Resonator assembly 110, shown in FIG. 3, is much the same as assembly 10, but in this instance the resonant element 115, is not removable from housing 112. Accordingly, O-Rings 32 are replaced with a more robust seal 132, made of an annulus of resiliently deformable material that is permanently affixed in place. Assembly 10 can be made with resonant element 15 machined as all one piece or with nodal 24, upper mass 16 and lower mass 18 added to torsional spring 20.

Figure 4:
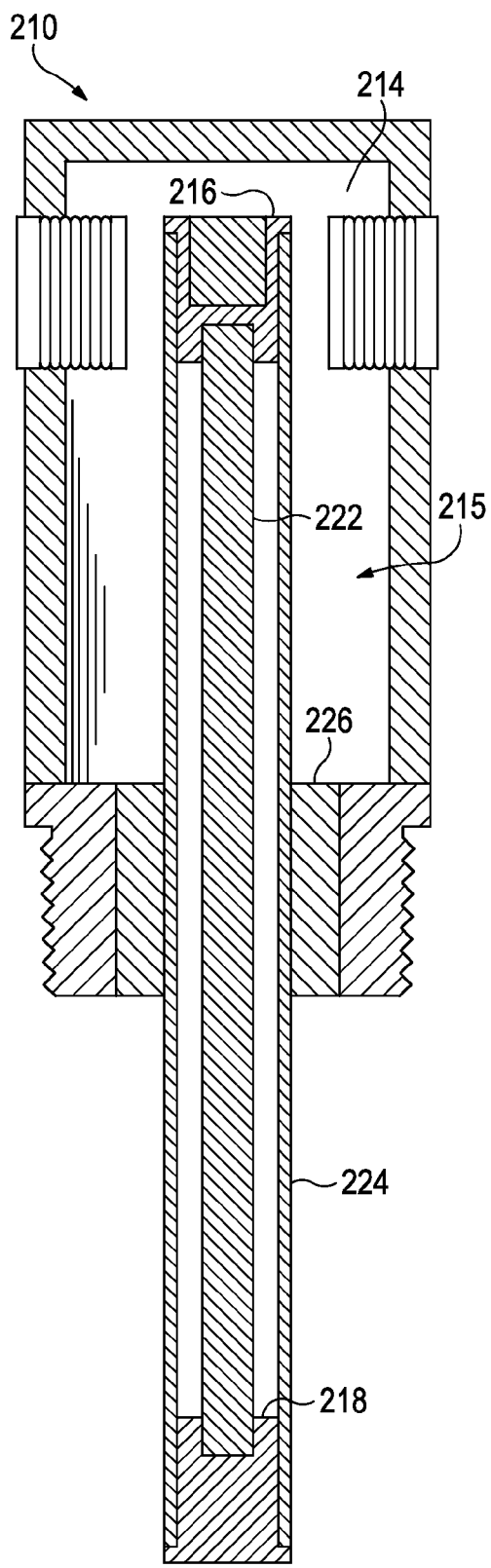
FIG. 4 is a vertical sectional view of an additional alternative embodiment of a resonant assembly.

Referring to FIG. 4, a resonator assembly 210 is similar to assemblies 10 and 110, except that the flexibility to permit torsion through a nodal support 226 that forms part of the seal of chamber 214, is provided by physical design of resonant element 215. An inner rod that serves as a torsion spring 222 is mounted in upper mass 216 and lower mass 218. In turn, masses 216 and 218 are mounted into an outer tube 224, which is sealed into nodal element 226. The torsional flexibility of rod 222 and tube 224 permits the coupled torsional flexure of masses 216 and 218; the tube 224 being rigidly affixed inside rigid nodal element 226.

Figure 5:
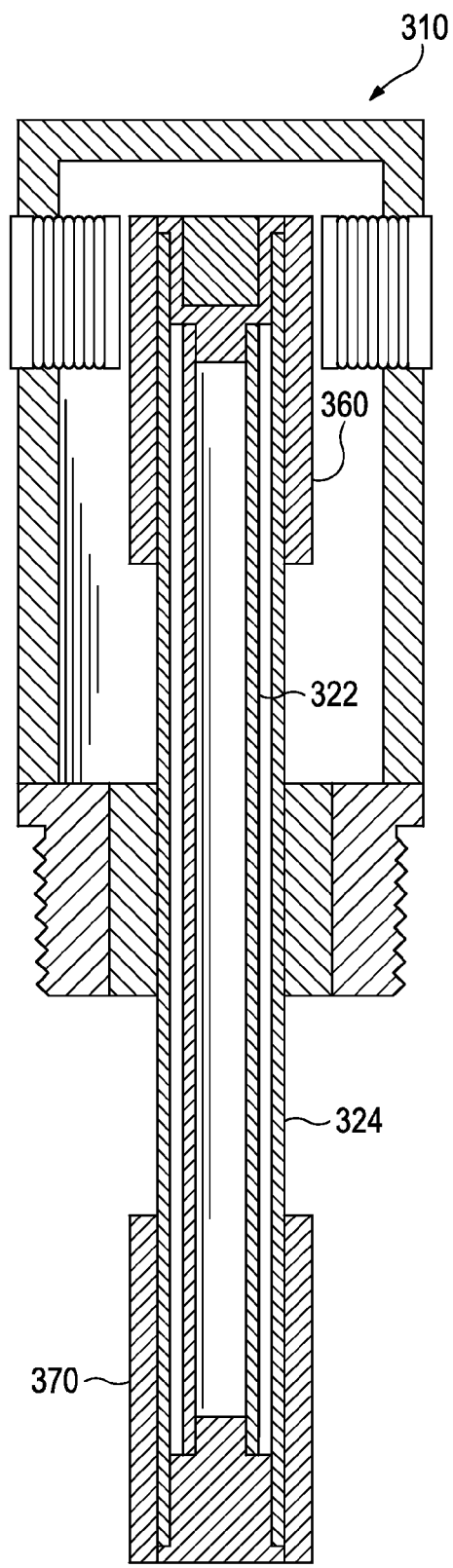
FIG. 5 is a vertical sectional view of a further alternative embodiment of a resonant assembly.

Referring to FIG. 5, resonator assembly 310 is much like assembly 210, but instead of having a central rod 222, assembly 310 has a central or inner tube 322. Tube 322 tends to be more naturally flexible than rod 222, and its characteristics can be chosen to achieve a desired effect. Also, exterior masses 360 and 370 can also be chosen to achieve a desired effect.

The rotational inertia of a cylinder is proportional to the fourth power of its radius. Accordingly, embodiments having radially expanded cylinders for masses 16 and 18 are dominated by these cylinders and the resonant frequency is determined by the spring constant of the torsional spring 20 and the rotational inertia of the end masses 16 and 18. Such a system is referred to as a "lumped constant" system. The lumped constant systems 10, 110, 310 and 410 provide greater design flexibility and can be made to have a relatively low resonant frequency. Embodiment 210, is a "distributed constant" system, and by contrast, must be made longer than a similar lumped constant system to have a comparably low resonant frequency. It is well known that the shearing of a fluid by a torsional resonator takes place in a boundary layer the thickness of which is inversely related to the frequency of vibrations. A thicker boundary layer can be advantageous for measuring properties of inhomogeneous fluids, such as emulsions and suspensions.

Figure 6:
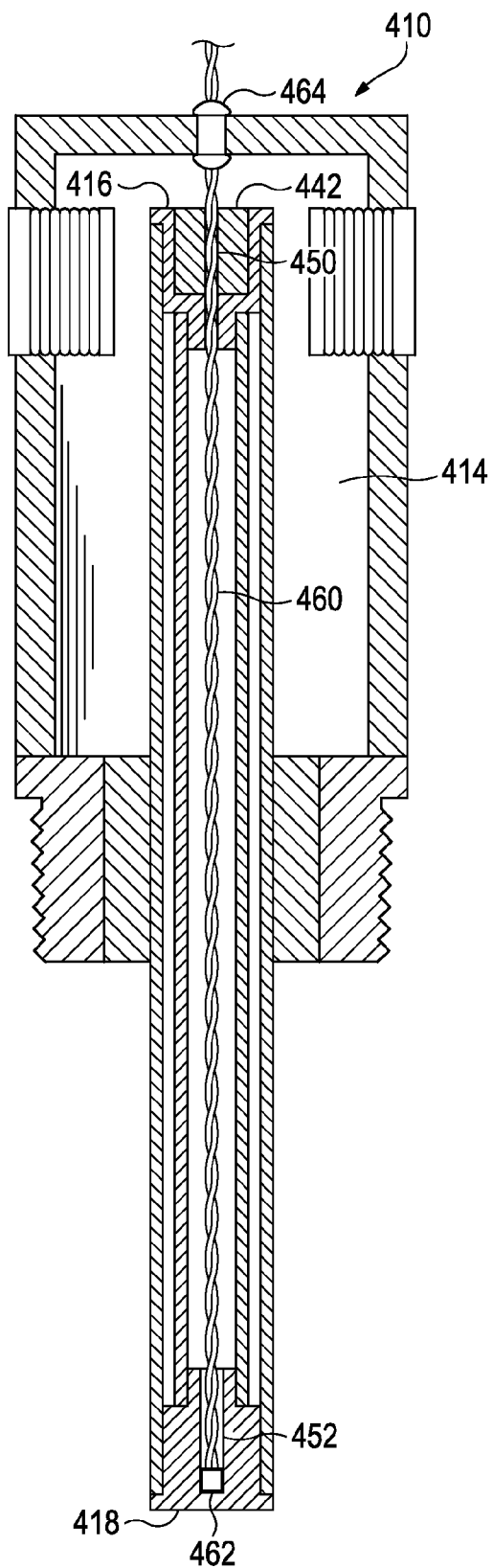
FIG. 6 is a vertical sectional view of a further alternative embodiment of a resonant assembly.

Resonator assembly 410, shown in FIG. 6, is similar to assembly 310, but having a longitudinal space 450 defined in magnet assembly 442 and mass 416, and another space 452 defined in bottom mass 418, thereby accommodating a twisted wire pair 460, connected to an electrical temperature measurement device 462. In one preferred embodiment device 462 is a platinum resistance thermometer, whereas in another preferred embodiment device 462 is a thermocouple welded into the end of mass 418. A sealing element 464 permits wire pair 460 to exit, while keeping fluids out of the chamber 414.

Outer tubes 224 and like elements that are exposed to the fluid being measured, are typically made of stainless steel, such as 316 stainless steel, to avoid damage from corrosion. Interior parts may be made of stainless steel, brass, ceramic, or any material with low and well-characterized intrinsic damping characteristics.

Assembly such as 10 preferably resonates in an anti-symmetric mode, in which second mass 18 vibrates in 180 degree opposite phase to first mass 16. When in anti-symmetric mode, nodal support 24 is situated at the natural node of the resonator. There is a degenerate symmetric mode, however, in which first mass 16 and second mass 18 vibrate in phase with one another. In the symmetric mode, nodal support 24 is not at a natural node of the resonator and the connection to the housing acts to damp the resonant element 15, leading to a false reading. Assembly 10 is carefully designed so that the frequency of the symmetric mode is sufficiently far from the frequency of the anti-symmetric mode, that the influence of the fluid is very unlikely to cause accidental excitation of the symmetric mode. To further protect the system, the frequency is checked regularly and if it enters a band defined around the symmetric mode, then system excitation is stopped and restarted, to bring resonant element 15 vibration back to the anti-symmetric mode.

Among the advantages of these embodiments 10, 110, 210, 310 and 410 is that they provide a well contained resonant system, with little energy leakage through mounting threads 30 because of the balanced resonant element 15. Accordingly, the details of installation make little difference to the operation, and therefore accuracy, of the resonant assembly.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A fluid properties measurement device, including:
   (a) a symmetric resonant element having a first mass and a second mass, balanced to said first mass and coupled to said first mass by a torsional spring, having a nodal support between said first mass and said second mass, said torsional spring further including a radially central element, having an outer surface, and a radially outer element, having an inner surface, mutually separated by a void defined by said outer surface and said inner surface, and joined together at its longitudinal ends;
   (b) a chamber having at least one opening and accommodating said first mass, free of mechanical constraint;
   (c) a driving and sensing assembly, adapted to drive said first mass in torsion and sense resulting torsional movement of said first mass;
   (d) wherein said torsional spring passes through said opening which is sealed about said torsional spring at said nodal support; and
   (e) wherein said second mass is free to be placed into a fluid, for fluid property measurements.

2. The device of claim 1, wherein said opening is sealed about said nodal support with a material that is resiliently deformable.

3. The device of claim 1, wherein said torsion spring is circular in cross-section.

4. The device of claim 1, wherein said first mass and said second mass are circular in cross-section.

5. The device of claim 1, wherein said radially central element is hollow.

6. The device of claim 1, wherein said radially central element is solid.

7. The device of claim 1, wherein said symmetric resonant element is cylindrical, thereby defining a cylinder, and wherein said first mass and said second mass are defined as portions of said cylinder.

8. The device of claim 1, wherein said first mass and said second mass are expanded in transverse dimension relative to said torsional spring.

9. The device of claim 1, wherein said driving and sensing assembly includes at least one permanent magnet attached to said symmetric resonant element and at least one electromagnetic coil positioned to apply force to said at least one permanent magnet.

10. A fluid properties measurement device, including:
   (a) a symmetric resonant element having a first mass and a second mass, balanced to said first mass and coupled to said first mass by a torsional spring, and having a nodal support between said first mass and said second mass;
   (b) a driving and sensing assembly, adapted to drive said first mass in torsion and sense resulting torsional movement of said first mass;
   (c) wherein said symmetric resonant element defines a longitudinal passageway from near to the longitudinal end of said second mass to exit point from said first mass;
   (d) electrical conductors passing through said passageway and out of said exit point; and
   (e) wherein an electrical temperature measurement device is placed in said second mass and is connected to said electrical conductors, thereby providing an electrical signal reflective of a temperature through said exit point.

11. The device of claim 10, wherein said electrical temperature measurement device is a thermocouple.

12. The device of claim 10, wherein said electrical temperature measurement device is a resistance thermometer element.

13. A fluid properties measurement device having a resonator capable of resonating in a preferred anti-symmetric mode, having a first resonant frequency, said device driving said resonator to resonate in a first frequency band about said first resonant frequency, but which may be caused to resonate in a symmetric mode, under some loading scenarios, said symmetric mode having a second resonant frequency that is significantly different from said first resonant frequency and wherein said device detects frequencies within a second frequency band about said second resonant frequency, and stops and restarts said driving of said resonator when a frequency in said second frequency band is detected.

14. The device of claim 13, wherein said resonator is symmetric and has a first mass and a second mass, balanced to said first mass and coupled to said first mass by a torsional spring, having a nodal support between said first mass and said second mass.

* * * * *